(12) United States Patent
Chirikjian et al.

(10) Patent No.: US 6,548,247 B1
(45) Date of Patent: Apr. 15, 2003

(54) DETECTION AND MAPPING OF POINT MUTATIONS USING PARTIAL DIGESTION

(75) Inventors: Jack G. Chirikjian, Potomac, MD (US); Leonard S. Bazar, North Potomac, MD (US)

(73) Assignee: Trevigen, Inc., Gaithersburg, MD (US)

( * ) Notice: Subject to any disclaimer, the term of this patent is extended or adjusted under 35 U.S.C. 154(b) by 0 days.

(21) Appl. No.: 09/402,959

(22) PCT Filed: Apr. 15, 1998

(86) PCT No.: PCT/US98/06878

§ 371 (c)(1),
(2), (4) Date: Dec. 9, 1999

(87) PCT Pub. No.: WO98/46793

PCT Pub. Date: Oct. 22, 1998

Related U.S. Application Data

(60) Provisional application No. 60/043,184, filed on Apr. 16, 1997.

(51) Int. Cl.[7] .............................. C07H 21/04; C12Q 1/68
(52) U.S. Cl. ....................... 435/6; 435/91.1; 536/23.1; 536/24.1; 204/450
(58) Field of Search ................... 435/6, 91.1; 536/23.1, 536/24.3; 204/450

(56) References Cited

U.S. PATENT DOCUMENTS

| | | | | |
|---|---|---|---|---|
| 5,763,178 A | * | 6/1998 | Chirikjian et al. | 435/6 |
| 5,851,770 A | * | 12/1998 | Babon et al. | 435/6 |
| 5,958,692 A | * | 9/1999 | Cotton et al. | 435/6 |
| 6,046,039 A | * | 4/2000 | Wong | 435/91.1 |

FOREIGN PATENT DOCUMENTS

| | | |
|---|---|---|
| WO | 93/20233 | 10/1993 |
| WO | 96/35809 | 11/1996 |
| WO | 96/40902 | 12/1996 |
| WO | 97/09444 | 3/1997 |
| WO | 97/12061 | 4/1997 |

OTHER PUBLICATIONS

Smith et al. "A simple method for DNA restriction site mapping" Nucleic Acids Research, vol. 3, No. 9, p. 2387–2398, Sep. 1976.*
Monnat et al. "Molecular analysis of human hpt Gene deletions and duplications" Adv. Exp. Med. Biol. 309B (purine Pyrimidine Metab. Man 7, Pt. B) p. 113–116, 1991.*
Hsu "Use of Mut Y and Thymine glycoselase to detect point mutations" Lab. Methods. Dect. Mutations Polymorphisms DNA, p. 195–205, 1997.*
D. R. Bentley et al., "Rapid Methods for Detection of Polymorphic Markers in Genomic DNA", Methods in Molecular Biology, vol. 9, 1/91, pp. 51–68.
K. J. Danna, "Determination of Fragment Order through Partial Digests and Multiple Enzyme Digests," Methods in Enzymology, vol. 65, 1980, pp. 449–467.
Ih–Chang Hsu et al., "Detection of DNA point mutations with DNA mismatch repair enzymes", Carcinogenesis, vol. 15:8, 1994, pp. 1657–1662.
A–Lien Lu et al., "Detection of Single DNA Base Mutations with Mismatch Repair Enzymes", Genomics, vol. 14, 1992, pp. 249–255.
Jing–Fan Xu et al., "Determining the site and nature of DNA mutations with the cloned MutY mismatch repair Enzyme", Carcinogenesis, vol. 17:2, pp. 321–326.
M. Yao et al., "Strand–specific Cleavage of Mismatch–containing DNA by Deoxyinosine 3'Endonuclease from *Escherichia coli*", J. Biol. Chemistry, vol. 209:50, 1994, pp. 31390–31396.
Rima Youil et al., "Screening for mutations by enzyme mismatch cleavage with T4 endonuclease VII", Proc. Natl. Acad. Sci., vol. 92, 1995, pp. 87–91.

* cited by examiner

*Primary Examiner*—Jeffrey Fredman
*Assistant Examiner*—Jeanine Goldberg
(74) *Attorney, Agent, or Firm*—Foley & Lardner

(57) ABSTRACT

According to the present invention there is provided a method for detecting the presence of at least two point mutations in a target polynucleotide, as well as their relative positions and specific nucleotide positions, involving partial digestion and the use of mismatch repair enzymes.

25 Claims, 3 Drawing Sheets

FIG. 3

```
ATG GAT GAT GCT ACT AAT AAA AAA AGG AAA GTC TTC GTT AGC ACC ATA   48
Met Asp Asp Ala Thr Asn Lys Lys Arg Lys Val Phe Val Ser Thr Ile
 1               5                  10                  15
CTT ACG TTT TGG AAT ACA GAT AGG CGC GAC TTT CCT TGG AGG CAT ACG   96
Leu Thr Phe Trp Asn Thr Asp Arg Arg Asp Phe Pro Trp Arg His Thr
                 20                  25                  30
AGG GAC CCC TAT GTA ATT TTA ATA ACG GAA ATC CTA CTT CGC AGG ACA  144
Arg Asp Pro Tyr Val Ile Leu Ile Thr Glu Ile Leu Leu Arg Arg Thr
             35                  40                  45
ACT GCG GGG CAT GTT AAA AAG ATA TAT GAC AAG TTT TTT GTT AAG TAC  192
Thr Ala Gly His Val Lys Lys Ile Tyr Asp Lys Phe Phe Val Lys Tyr
         50                  55                  60
AAG TGC TTT GAG GAT ATA TTA AAA ACG CCA AAA TCA GAA ATC GCC AAA  240
Lys Cys Phe Glu Asp Ile Leu Lys Thr Pro Lys Ser Glu Ile Ala Lys
 65                  70                  75                  80
GAC ATA AAA GAA ATC GGA CTC TCT AAC CAA AGG GCA GAA CAG CTA AAA  288
Asp Ile Lys Glu Ile Gly Leu Ser Asn Gln Arg Ala Glu Gln Leu Lys
                 85                  90                  95
GAA CTG GCA AGG GTC GTC ATA AAT GAT TAT GGG GGC AGA GTG CCC CGA  336
Glu Leu Ala Arg Val Val Ile Asn Asp Tyr Gly Gly Arg Val Pro Arg
             100                 105                 110
AAT AGG AAG GCA ATT TTA GAT CTA CCA GGA GTT GGC AAA TAC ACT TGT  384
Asn Arg Lys Ala Ile Leu Asp Leu Pro Gly Val Gly Lys Tyr Thr Cys
         115                 120                 125
GCT GCA GTT ATG TGT TTG GCA TTT GGC AAA AAA GCC GCT ATG GTC GAT  432
Ala Ala Val Met Cys Leu Ala Phe Gly Lys Lys Ala Ala Met Val Asp
 130                 135                 140
GCA AAT TTT GTG AGA GTT ATT AAC AGG TAC TTT GGG GGA AGC TAT GAA  480
Ala Asn Phe Val Arg Val Ile Asn Arg Tyr Phe Gly Gly Ser Tyr Glu
145                 150                 155                 160
AAC CTG AAC TAC AAC CAC AAG GCC CTG TGG GAA CTT GCG GAG ACC CTT  528
Asn Leu Asn Tyr Asn His Lys Ala Leu Trp Glu Leu Ala Glu Thr Leu
                 165                 170                 175
GTA CCT GGC GGA AAG TGC AGG GAC TTT AAC CTT GGT TTA ATG GAC TTT  576
Val Pro Gly Gly Lys Cys Arg Asp Phe Asn Leu Gly Leu Met Asp Phe
             180                 185                 190
TCC GCA ATC ATA TGT GCC CCA AGA AAG CCA AAG TGT GAG AAA TGT GGG  624
Ser Ala Ile Ile Cys Ala Pro Arg Lys Pro Lys Cys Glu Lys Cys Gly
         195                 200                 205
ATG AGC AAA CTC TGT AGC TAC TAT GAG AAG TGT AGT ACT TGA           666
Met Ser Lys Leu Cys Ser Tyr Tyr Glu Lys Cys Ser Thr  *
 210                 215                 220
```

DETECTION AND MAPPING OF POINT MUTATIONS USING PARTIAL DIGESTION

CROSS REFERENCE TO RELATED APPLICATIONS

This application is a 371 of PCT/US98/06878, filed Apr. 15, 1998. This application also claims priority to U.S. Provisional application No. 60/043,184, filed Apr. 16, 1997.

FIELD OF THE INVENTION

The present invention relates to a method for detecting the presence of at least two point mutations in a target polynucleotide, as well as their relative positions and specific nucleotide position, via partial digestion. The present invention further relates to a method for detecting the presence of at least two point mutations in a target polynucleotide, as well as their relative positions and specific nucleotide position via a combination of partial digestion and an oscillation reaction.

BACKGROUND OF THE INVENTION

Genomic DNA provides the template for the information that allows the generation of proteins which are expressed and made by an organism. These proteins are generally essential for the survival of any specific cell in an organism. Therefore, the organism requires the template to be correct and free of mistakes in order to generate a protein that is functional in a cell. The protein may be nonfunctional if a single nucleotide of this DNA sequence is mutated ("a point mutation"). Point mutations which elicit disease states are known for many proteins.

Recent advances have allowed for the detection of point mutations with mismatch repair enzymes. Hsu et al., *Carcinogenesis* 15: 1657 (1994), describe the detection of A/G point mutations with mutY repair enzyme. Xu et al., *Carcinogenesis* 17(2): 321 (1996) further describe using mutY to detect A/G and to a lesser extent C/A mutations.

Youil et al., *PNAS* 92: 87 (1995) relate techniques for screening for each of the possible eight point mutations i.e. G/A, C/T, C/C, G/G, A/A, T/T, C/A, and G/T, using T4 endonuclease VII. Lu et al., WO93/20233 at 29–30 describe screening for mutations using all-type enzyme, which recognizes all eight base pair point mutations. Lu et al. also describe the use of combinations of different repair enzymes to ascertain the presence of an unknown point mutation in a sample. Id. at 27.

These techniques are directed, however, to the detection of a single point mutation in a given polynucleotide sample. To the extent that a nucleic acid target molecule has multiple base pair mutations spanning its length, the above methods are either ineffective or inefficient in detecting the presence and relative position of these mutations.

WO 96/40902 is also a background publication.

SUMMARY OF THE INVENTION

It is therefore an object of the present invention to provide a method for detecting the presence of at least two point mutations in a target polynucleotide, as well as their relative positions and specific nucleotide position via partial digestion.

It is a further object of the present invention to provide a method for detecting the presence of at least two point mutations in a target polynucleotide, as well as their relative positions and specific nucleotide position via a combination of partial digestion and an oscillation reaction.

In accomplishing the foregoing objects as well as other objects, there is provided a method of detecting the presence of and determining the relative positions of at least two point mutations in target polynucleotides, comprising:
 (a) hybridizing single-stranded oligonucleotide probes to target polynucleotides to form hybrid, double-stranded polynucleotides such that mismatches occur at the sites of the point mutations, wherein the probes are complementary to a non-mutated sequence of the target polynucleotides and are labelled-at one end but not both ends, and wherein the target polynucleotides are not labelled;
 (b) partially digesting the probe strands of the hybrid polynucleotides with a nucleic acid repair enzyme such that probe fragments of differing lengths are generated;
 (c) separating the probe fragments by size in a medium suitable for visualizing the separated probe fragments; and then
 (d) visualizing the separated probe fragments in the medium, whereby the presence and relative positions of the point mutations are determined.

There is further provided a method of detecting the presence of and determining the relative positions of at least two point mutations in a target polynucleotide, comprising:
 (a) hybridizing a single-stranded oligonucleotide probe to a target polynucleotide to form a hybrid, double-stranded polynucleotide such that mismatches occur at the sites of the point mutations, wherein the probe is complementary to a non-mutated sequence of the target polynucleotide and is labelled at one end but not both ends, and wherein the target polynucleotide is not labelled;
 (b) partially digesting the probe strand of the hybrid polynucleotide with a nucleic acid repair enzyme producing oligonucleotide fragments, wherein the oligonucleotide probe is designed such that the oligonucleotide fragments dissociate from the target polynucleotide spontaneously at a predetermined temperature;
 (c) repeating steps (a) and (b) such that probe fragments of differing lengths are generated;
 (d) separating the probe fragments by size in a medium suitable for visualizing the separated probe fragments; and then
 (e) visualizing the separated probe fragments in the medium, whereby the presence and relative positions of the point mutations are determined.

BRIEF DESCRIPTION OF THE DRAWINGS

FIG. 3 is a representation of the DNA sequence of orf10 and the amino acid sequence of the corresponding ORF10 polypeptide (SEQ ID NOS 9 and 10).

DETAILED DESCRIPTION OF PREFERRED EMBODIMENTS

Figure 1:
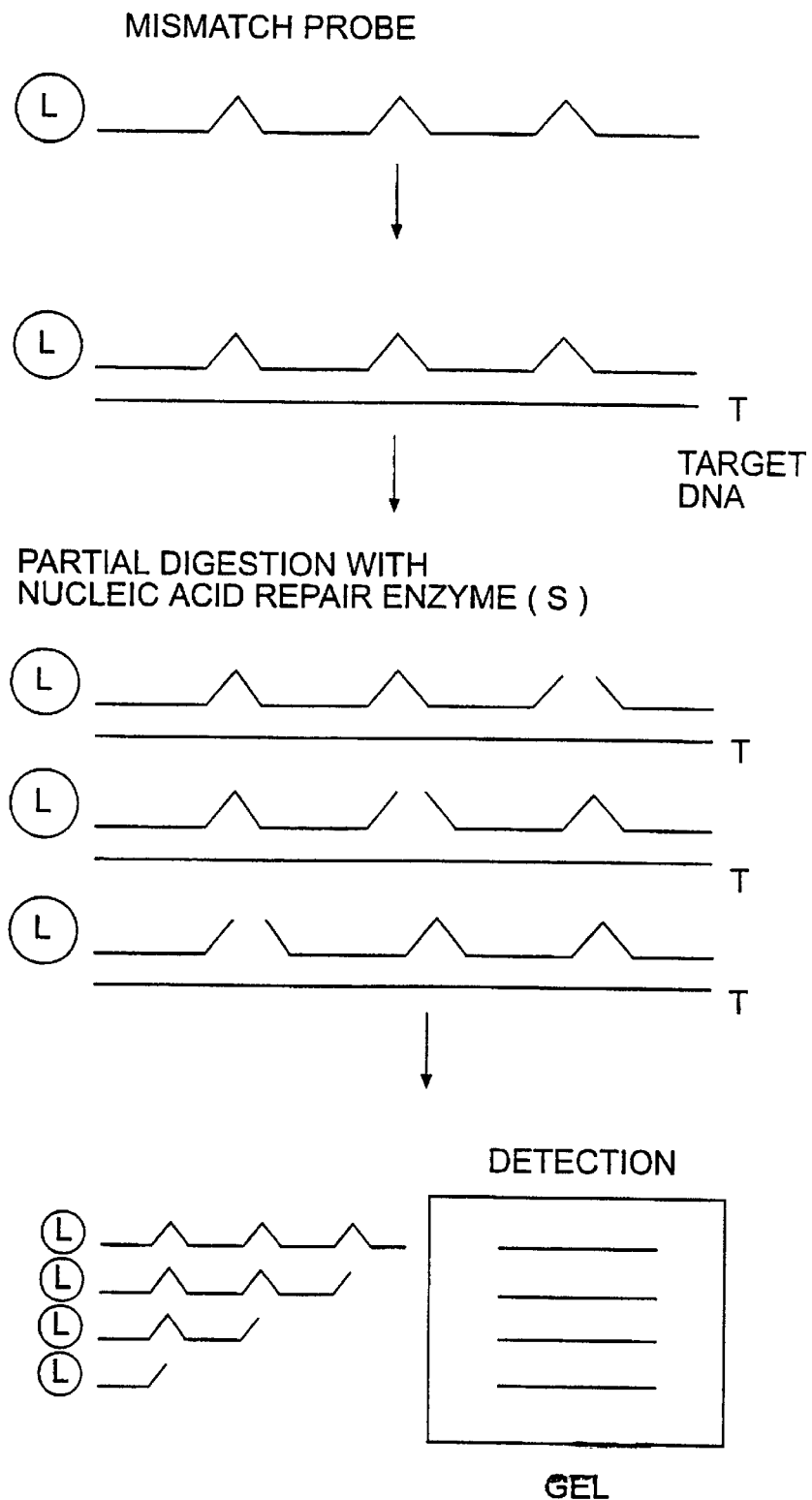
FIG. 1 is a schematic diagram showing the detection of three point mutations using the partial digestion method of the instant invention. Probe is hybridized to target and then nucleic acid repair enzyme is added, which partially digests the probe. The resulting probe fragments are then detected.
Figure 2:
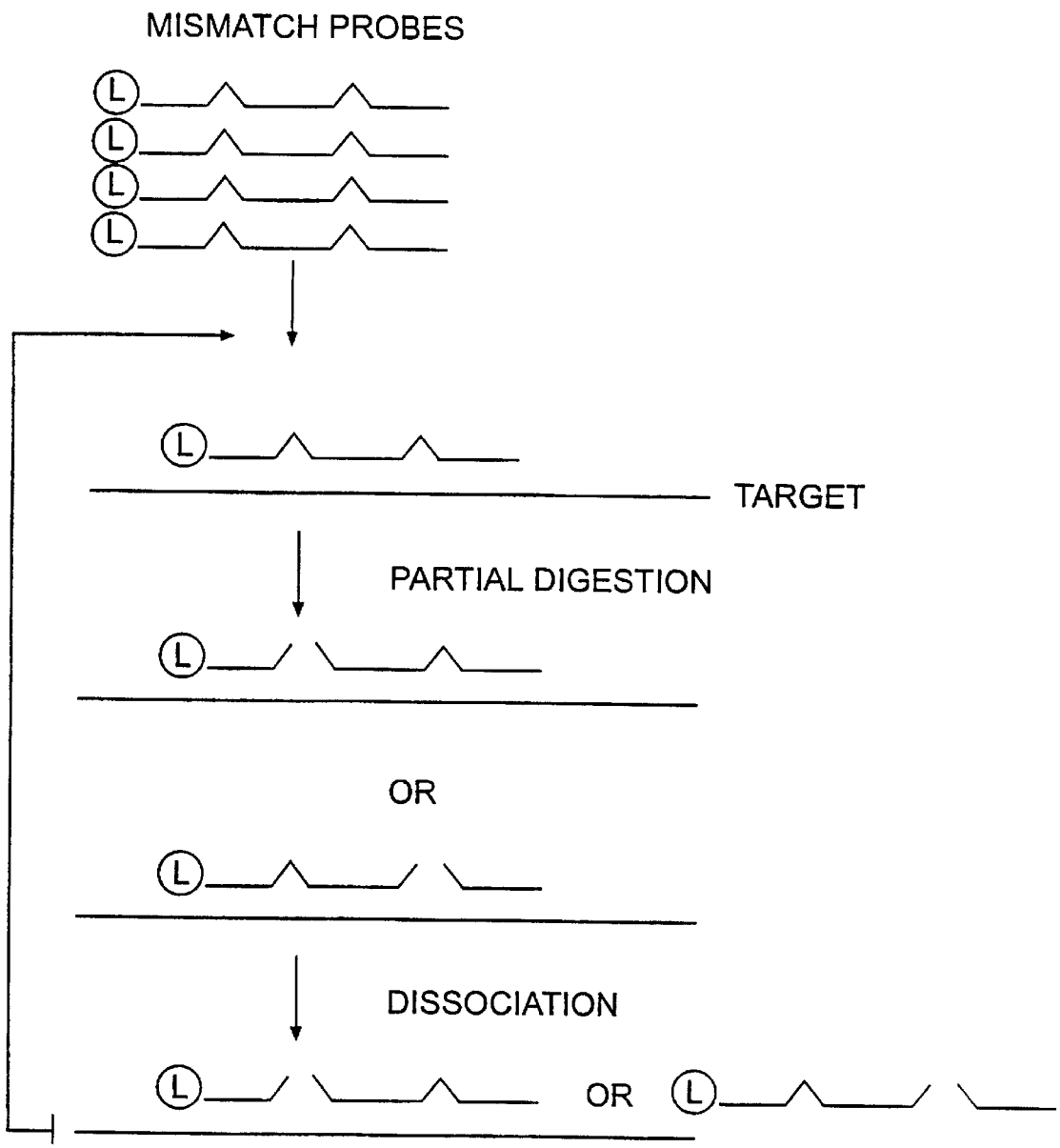
FIG. 2 is a schematic diagram showing the detection of two point mutations using partial digestion in combination with an oscillation reaction. Probe is hybridized to target and then nucleic acid repair enzyme is added, which partially digests the probe. The probe then dissociates from the target, with or without an increase in temperature, and the cycle is repeated.

The above-mentioned disadvantages of conventional techniques for detecting multiple point mutations have been overcome by the present invention. In particular, it has been discovered that partial digests, effected using mismatch repair enzymes, allow for the detection and mapping of multiple base pair mutations.

Partial digest mapping has been limited heretofore to restriction endonucleases. For example, see Danna et al., 65 METHODS IN ENZYMOLOGY, Ch. 53, at page 449 (Academic Press 1980). Restriction endonucleases are not desirable for detecting multiple point mutations, however, because a restriction enzyme can only detect a mutation if it is located within the enzyme's specific cleavage recognition site.

The instant invention therefore has overcome the above-mentioned disadvantages of existing techniques for detecting point mutations. The inventive approach entails hybridizing single-stranded oligonucleotide probes to target polynucleotides to form hybrid, double-stranded polynucleotides. The hybridization preferably occurs under conditions that are "stringent," which typically implicates conditions that include a 50–100 mM salt solution at a temperature of (3N—20° C.), where N is the number of nucleotides in the oligonucleotide probe.

As for probe design, preferably, the oligonucleotide probe is designed not to have self complementary regions, palindromic regions and the probe must also have probe specificity. The parameters for probe design can be found in Lowe et al., *Nucl. Acids Res.* 18:1757–1761 (1990); Rychlik et al., *loc. cit.* 17:8543–8551 (1989); Rychlik et al., *loc. cit.* 18:6409–6412 (1990), which discusses probe design as applied to PCR reactions.

The probe may be a synthetic oligonucleotide, or may be derived from the PCR amplification of a desired genomic DNA or cDNA sequence by amplifying the desired sequence with two primers one of which is labelled. The probe may also be a restriction fragment generated from restriction endonuclease cleaving of a desired genomic DNA or cDNA sequence.

The oligonucleotide probe also is labelled. Probe labelling allows for the detection of cleaved oligonucleotide fragments and may be accomplished by a number of art recognized methods. For example, the oligonucleotide can be tagged with a radioactive label, such as a radiolabelled nucleotide. Alternatively, the probe can be labelled with biotinylated nucleotides or florescent nucleotides as known to those of skill in the art.

In the present invention, the oligonucleotide probe is labelled at one end but not both. Additionally, the target polynucleotide is not labelled.

Because the probe is complementary to a non-mutated sequence of the target polynucleotide, there will be mismatches between non-mutated probe and mutated target polynucleotides at each site of point mutation. In the instant invention, the target polynucleotide will have at least two mismatch sites.

The probe strands of the hybrid probe-target polynucleotides are then partially digested with a "nucleic acid repair enzyme," such that probe fragments of differing lengths are generated. The probe fragments are then separated by size in a medium suitable for visualizing the separated fragments. The separated fragments are then visualized, and the presence and relative position of the point mutations are determined.

In a further embodiment, the size of the separated probe fragments are measured and thereby the specific nucleotide position of each point mutation is determined. Methods for measuring the size of nucleotide bands in visualizing medium are known to those of skill in the art. For example, a size marker can be used to determine the size of a nucleotide band in an electrophoresis gel.

The phrase "polynucleotide target" is used here to denote a nucleotide sequence of any size, including a sequence of less than 30 base pairs, or up to several hundred base pairs. For instance, examples of polynucleotide targets include the genes or portions of genes which have been isolated from genomic or CDNA libraries by methods known to the skilled artisan, such as PCR amplification. In particular, genes of interest would be those known to exhibit point mutations eliciting disease states. Examples include sickle cell anemia hypoxanthine phosphotransferase and p53, a tumor suppressor gene, as well as several oncogenes and cancer genes. Other illustrations of polynucleotide targets include cDNAs generated by reverse transcriptase, and a specific deoxyoligonucleotide primer encompassing a short sequence immediately downstream of a hotspot for mutations within a gene such as BRCA1.

Other examples of polynucleotide targets include cDNAs prepared by reverse transcriptase using mRNA as template and a deoxynucleotide primer specific for the mRNA of interest. In this case the cDNA would act as a target for a labelled oligonucleotide to generate a base mismatch or several base mismatches upon hybridization. The addition of DNA mismatch repair enzymes would result in the formation of cleaved products whose intensity could allow for the quantitation of the mRNA or to determine if the genomic DNA encoding this mRNA has one or more point mutations.

In fact, this procedure can act as an endogenous method for amplifying a target gene, such as BRCA1, in that a cell's own production of mRNA produces a desired amount of target polynucleotide for a partial digestion assay. Detection of point mutations within target cDNAs by this embodiment can therefore obviate the need for amplification by PCR.

Another example of a polynucleotide target includes bacterial 16S rRNA genes and intergenic regions. See Brow et al., *J. Clin. Microbiol.* 34:3129–3137 (1996). In this scenario, a 350 bp segment of *E. coli* 16S rRNA DNA is amplified by PCR using a labelled primer and an unlabelled primer. The labelled PCR product, labelled at one end on one of the strands, is mixed with a target DNA from an unknown bacterium comprising a PCR product generated with the same unlabelled primers. Denaturation and renaturation of the target and probe DNAs generates a proportion of molecules in which the labelled strand comes from the *E. coli* and the other strand comes from the unknown bacterium. A number of base mismatches are created between the two strands which are cleaved by the DNA mismatch repair enzymes. The cleaved products are detected on a denaturing polyacrylamide gel or by other methods known to the skilled artisan. The pattern of the cleavage products would be characteristic of the sequence of the unknown bacterium's 16S rRNA gene and could therefore be a means of identification of the unknown organism.

In the present description, the phrase "nucleic acid repair enzyme" denotes an enzyme that cleaves, at a point of mismatch, one strand of a duplex formed by oligonucleotide probe and target polynucleotide. Examples of nucleic acid repair enzymes which can be used in the above process are mutY (Wu et al., *Proc. Nat'l Acad. Sci. USA* 89: 8779–83 (1992)), T/G mismatch-specific nicking enzyme from HeLa nuclear extracts (Wiebauer & Jiricny, *Nature* 339: 234–36 (1989); Wiebauer & Jiricny, *loc. cit.* 87: 5842–45 (1990)), T/G mismatch-specific nicking enzyme from *E. coli* (Hennecke et al., *Nature* 353:

776–78 (1991)), human yeast all-type enzymes (Yeh et al., *J. Biol. Chem.* 2667: 6480–84 (1991); Chiang & Lu, *Nuc. Acids Res.,* 19:4761–4766 (1981)), Deoxyinosine 3'-Endonuclease from *E. coli* (Yao et al., *J. Biol. Chem.* 270: 28609–16 (1995); Yao et al., *J. Biol. Chem.* 269: 31390–96 (1994)).

Another example of nucleic acid repair enzyme is an enzyme system comprising a glycosylase combined with an AP cleaving enzyme, such as endonuclease or lyase. Together glycosylase and AP cleaving enzyme, such as endonuclease or lyase cleave oligonucleotide probe/target polynucleotide duplex at a point of mismatch. A glycosylase creates an abasic sugar (an AP site) at the point of mismatch, which then is cleaved by an AP cleaving enzyme, such as endonuclease or lyase. Illustrative enzymes in these categories are detailed below:

I. glycosylases—tag-1, alkA, ung, fpy, muty, nth, xthA, nfo, recJ, uvtA, uvrD, mfd, mutH, mutL, mutS, uracil DNA glycosylase, hydroxymethyluracil glycosylase, 5-mC DNA glycosylase, hypoxanthine DNA glycosylase, thymine mismatch DNA glycosylase, 3-mA DNA glycosylase, hydrated thymine DNA glycosylase (endonuclease III), pyrimidine dimer glycosylase. These enzymes can come from any different biological sources. For example, Friedberg et al., DNA REPAIR AND MUTAGENESIS (ASM Press 1995), lists uracil DNA glycosylases from herpes simplex virus types 1 and 2, equine herpes virus, Varicella zoster virus, Epstein Barr virus, human cytomegalovirus, *Mycoplasma lactucae, E. coli, B. subtilis, M. luteus, B. steorophermaophilus, Thermothrix thirpara, S. pneumoniae, Dictyostelium discoideium, Artenia salina, S. cerevisae, Hordeum vulgare, Zea mays, Triticum vulgare,* rat liver mitochondria, calf thymus, human placenta, HeLa S3 cells, and acute leukemia blast cells.

II. AP cleaving enzymes—*E. coli* exonuclease III, *E. coli* endonuclease IV, Saccharomyes AP endonuclease, *Drosphila melanogaster* AP endonuclease I and II, human AP endonuclease, human AP lyase, BAP endonuclease, APEX endonuclease, HAP1 and AP endonuclease.

In addition to the above systems, cleavage may also be effected by using a glycosylase enzyme, as described above, in combination with basic conditions and increased temperature. In this embodiment, increasing pH and temperature effectuates cleavage at the AP site created by the glycosylase enzyme. Suitable parameters for cleavage of the AP site are pH levels of approximately 8 to 14, and temperatures ranging from approximately 50° to 95° C.

In another embodiment, the present invention employs a nucleic acid repair enzyme that is thermally stable, in the sense that the enzyme would function at some elevated temperature, such as from 50° to 80° C. Additionally, it is preferable that the thermally stable nucleic acid repair enzyme withstand temperatures up to 100° C. for short periods.

For instance, the present invention contemplates the use of a thermally stable glycosylase. An example of a thermally stable glycosylase is the ORF10 protein encoded by the DNA sequence of FIG. 3. This enzyme has been synthesized by Richard P. Cunningham at the State University of New York at Albany, according to the methods of Example 4. See also Horst et al., *EMBO J.* 15: 5459 (1996).

The substrate activity of the ORF10 enzyme includes both base cleaving properties and AP endonuclease activities. The AP endonuclease activities of this enzyme may be enhanced, however, by changing the amino acid residue in position 126 of FIG. 1 from a tyrosine to a lysine. This substitution may be achieved by site directed mutagenesis by the methods discussed in Deng, et al., *J.A. Anal. Biochem.* 200:81 (1992).

The ORF10 glycosylase is a homologue of the endonuclease III family. As such, the skilled artisan may identify and isolate genes of the endonuclease III family from other thermophilic bacteria. Suitable probes may be designed as degenerate nucleotide coding sequences for the following amino acid sequences which are highly conserved amongst the members of the endonuclease III family: (SEQ ID NO:1), PYVILITEILLRRTT; (SEQ ID NO:2), AILDLPGVGKYT; (SEQ ID NO:3), MVDANFVRVINR.

These degenerate oligonucleotides may be used as PCR primers to amplify portions of the gene from the chromosomal DNA of thermophilic bacteria by PCR. Such amplified PCR products may then be used to screen a library of the thermophilic bacterium. Positive clones would be sequenced and the coding sequence for the mismatch glycosylase cloned into an expression vector for protein production.

Additionally, the present invention can utilize a combination of nucleic acid repair enzymes. For example, a nucleic acid repair enzyme can be used in combination with a AP cleaving enzyme. Advantageously, mutY is used in combination with AP cleaving enzymes, such as DNA lyase or DNA AP endonuclease. Such a system of enzymes enhances the speed at which cleavage occurs.

As for the method step of partially digesting probe strands, partial digestion techniques are known to those skilled in the art. See Danna, supra. For the purposes of the instant description, a partial digestion denotes a situation where a nucleic acid does not effectuate complete cleavage of all probes stands in a reaction.

For example, where there are two points of mismatch on the probe-target hybrid, a partial digestion with a nucleic acid repair enzyme will not cleave every probe-target hybrid at both points of mismatch. Instead, certain hybrids will be cleaved at the first point of mismatch, others will be cleaved at the second point of mismatch, and others still may be cleaved at both points.

A partial digestion can be established by various techniques known to those of skill in the art. For example, a partial digestion is obtained by limiting the reaction time so that the nucleic acid repair enzyme does not cleave at all possible recognition sites within the probe oligonucleotide. Other methods for establishing a partial digestion include serial dilutions of a reaction solution containing the enzyme or variation of the cation concentration in the solution.

The cleaved fragments resulting from the above-described partial digests are separated by size and visualized by methods known to those of skill in the art. Such methods include gel electrophoresis and capillary electrophoresis as described above. The length of the cleaved fragments can be measured and, and thereby the specific nucleotide position of each point mutation determined, by comparing the probe fragments to labelled DNA fragments of known size, as mentioned above.

In one embodiment of the present invention, the target polynucleotides and oligonucleotide probes have been amplified by techniques known to the skilled artisan, such as PCR, so that there is a sufficient amount of probe fragments to be visualized, after the probe fragments have been separated by size in a visualizing medium.

In another embodiment of the present invention an oscillation reaction is employed to obviate or diminish the need for amplified target polynucleotide. In particular, an oscillation reaction is created whereby a nucleic acid repair enzyme partially digests the oligonucleotide probe producing probe fragments which dissociate from the target polynucleotide at a predetermined temperature. That is, the oligonucleotide probe is designed so that, at the predetermined temperature, the oligonucleotide fragments dissociate from the target polynucleotide after cleavage by nucleic acid repair enzyme. A cycle or oscillation reaction then occurs because the target polynucleotide hybridizes to another oligonucleotide probe, and the cleavage process is repeated.

As a consequence, a small number of target polynucleotides can be detected in a sample, since a single target polynucleotide catalyses the formation of a large number of oligonucleotide probe cleavage fragments. The oscillation reaction can detect from 10–100 target polynucleotide molecules in a sample. Theoretically, the oscillation reaction may detect as little as one target polynucleotide molecule in a sample.

To accommodate the oscillation reaction, a high concentration of oligonucleotide probe is utilized. In this regard, a suitable radiolabelled probe concentration is from 0.01 to 10 pmol. Other concentrations can be used depending on the desired length of autoradiograph exposure times.

One of skill in the art can refer to Duck et al., *BioTechniques* 9(2): 142 (1990), which refers to CPT a similar but less advantageous technique for amplifying probe.

In one embodiment, the oscillating reaction is performed isothermally, i.e., the predetermined temperature of dissociation is approximately the same as, i.e., within a few degrees of, the temperature of hybridization. In a preferred embodiment, this isothermal temperature is 3N—20° C., here N is the length of the probe in base pairs. Within this working range the optimal temperature is determined empirically. Preferably, the reaction is performed with 0.01 to 10 pmol of labeled probe, in the presence of either synthetic target sequence or DNA purified from a sample source. This target DNA will ranges from 1 to $10^{12}$ molecules.

In another embodiment, the oscillation reaction is not carried out isothermally, but instead results from temperature cycling. In this embodiment, the hybridization is effectuated at a temperature which is lower than the temperature of dissociation. In other words, after probe has hybridized to the target polynucleotide, the reaction temperature is raised to a predetermined temperature to effectuate the dissociation of the probe fragments from the target polynucleotide. The reaction is then cooled to allow non-cleaved probe to hybridize to the target polynucleotide, and the cycle is repeated. At this stage, more nucleic acid repair enzymes can be added if needed, to the extent that the original enzymes have lost activity due to the increase of temperature. In a preferred embodiment, the temperature is raised to between 85° C. and 95° C. for 1–2 minutes to dissociate the cleaved probe fragments from the target polynucleotide. The reaction is then slowly cooled to approximately 20° C. to allow more non-cleaved probe to hybridize to the target polynucleotide, and the cycle is repeated.

In this preferred embodiment, an example of a preferred nucleic acid repair enzyme is thermophylic thymine DNA glycosylase, in particular, the enzyme is one encoded by the orf10 sequence of FIG. 3. This enzyme will survive several cycles of exposure to 85° C. for short periods.

In either of the above described isothermal or non-isothermal embodiments, hybridization can be facilitated by a helix destabilizing molecule. For instance, a helix destabilizing molecule can allow hybridization of a 20-mer synthetic oligonucleotide to target polynucleotide at 40° C.

By reducing the temperature necessary to achieve hybridization of oligonucleotide probe to target polynucleotide, helix destabilizing molecule can reduce the need for thermostable enzymes and expensive thermocyclers.

Exemplary helix-destabilizing molecules include *I, herpes simplex virus-type I ICP8, nucleolin, and adenovirus DNA-binding protein. See Topal & Sinha, *J. Biol. Chem.* 258(20): 12274–79 (1983); Alberts & Frey, *Nature* 227: 1313–18 (1970); Hosoda & Moise, *J. Biol. Chem.* 253(20): 7547–55 (1978); Ghisolfi et al., *loc. cit.,* 267(5): 2955–59 (1992); Boehmer & Lehman, *J. Virol.* 67(2): 711–15 (1993); Zijderveld & van der Vleit, *J. Virol.* 68(2): 1158–64 (1994); Monaghan et al., *Nucleic Acids Research* 22(5): 742–48 (1994).

When facilitated by helix-destabilizing molecule, hybridization in accordance with the present invention can be effected with long -synthetic oligonucleotides, without the use of thermostable enzymes or expensive thermocyclers. A "long" oligonucleotide in this context is greater than 25 nucleotides but preferably not greater than 100 nucleotides. Use of such long oligonucleotides affords the advantage of hybridizing to the target polynucleotide with increased specificity.

The presence of a helix-destabilizing molecule thus allows for the use of long synthetic oligonucleotides, without thermostable enzymes or expensive thermocyclers. The helix-destabilizing molecule allows for the dispensation of thermostable enzymes because it lowers the temperature necessary for hybridization.

The following examples merely illustrate the invention and, as such, are not to be considered as limiting the invention set forth in the claims.

EXAMPLE 1

Partial Digestion Detection and Mapping of Multiple Point Multiple Point Mutations within a DNA Sequence The following synthetic oligonucleotides WT CS and MUT NCS (SEQ ID NO:4 and SEQ ID NO:6) were synthesized using standard phosphoramidite chemistry, well known to those in the art.

```
5'-AAATGGAGTTATTCCAACAGATAAAGTGTTGAATGGAATACTTAGTTATCTTGGAATGACTAAAGTAGAATTAGA-3'     (WT CS)
3'-TTTACCTTAATAAGGTTGTATATTTCACAATTTACCTTATGAATTAATAGAACCTTAATGATTTCATTTTAATCT-³²P    (MUT NCS)
        I            II        III          IV            V          VI
```

$5'$-$^{32}$P-labeled wild type noncoding strand (WT NCS) or $5'$-$^{32}$P-mutated noncoding strand (MUT NCS) was annealed to the unlabeled wild type coding strand (WT CS). Mismatched bases in the NCS are underlined and numbered. Various amounts of thymine DNA glycosylase enzyme (Tdg), which removes the T at T/G mismatches or mutY enzyme, which cleaves the phosphodiester bond after the A at A/G mismatches were added and incubated for 1 hr at 55° C. and 37° C. for the Tdg and mutY enzymes, respectively. In some cases, *E. coli* Endo IV was added to a set of Tdg enzyme tubes to facilitate phosphodiester bond cleavage at T/G mismatches where the Tdg enzyme has removed the T. At the end of the incubation, the DNA was electrophoresed on a 20% denaturing polyacrylamide gel. The gel was exposed to X ray film for various periods of time.

With a short exposure, the Tdg enzyme detected T/G mismatches I and III. Mismatches III, IV, and VI were detected following a longer exposure.

EXAMPLE 2

Partial Digestion Detection and Mapping of Multiple Point Multiple Point Mutations within a DNA Sequence The following 75 base sequence of a mutated noncoding strand (NCS) (SEQ ID NO:5) was synthesized which generates two A/G and two T/G mismatches when hybridized to a wild type coding strand (CS):

```
5'-TCTAATTCTACTTTAGTAATTCCAAGATAATTAAGTATCCATTAAACACTTTATTTGTTGGAATAACTCCATTT-3' Mut NCS
                 4              3              2              1
```

The two A/G (numbers 2 and 4) and the two T/G mismatches (numbers 1 and 3), generated by hybridization of a labelled 75 base mutant probe (Mut NCS) to a wild-type target sequence (WT CS), were recognized by the DNA mismatch repair enzymes mutY and Tdg enzyme, respectively, at dilutions of 1:100 and 1:10, respective temperatures of 55° C. for Tdg and 37° C. for mutY and a 1 hour incubation time. As controls, hybridization of a $^{32}$P-labelled wild-type probe WT NCS to the same 75 base wild-type target WT CS polynucleotide failed to generate any mismatches and, therefore, no cleavage products were found.

EXAMPLE 3

Partial Digestion Detection and Mapping of Multiple Point Multiple Point Mutations within a DNA Sequence Combined with an Oscillation Reaction The following synthetic oligonucleotides, WT CS and MUT NCS (SEQ ID NO:4 and SEQ ID NO:6) is synthesized using standard phosphoramidite chemistry, well known to those in the art.

```
5'-AAATGGAGTTATTCCAACAGATAAAGTGTTGAATGGAATACTTAGTTATCTTGGAATGACTAAAGTAGAATTAGA-3'     (WT CS)
3'-TTTACCTTAATAAGGTTGTATATTTCACAATTTACCTTATGAATTAATAGAACCTTAATGATTTCATTTTAATCT-³²P   (MUT NCS)
       I           II         III              IV             V         VI
```

5'-$^{32}$P-labeled wild type noncoding strand (WT NCS) or 5'-$^{32}$P-mutated noncoding strand (MUT NCS) is annealed to the unlabeled wild type coding strand (WT CS). Mismatched bases in the NCS are underlined and numbered. Thymine DNA glycosylase enzyme (Tdg), which removes the T at T/G mismatches or mutY enzyme, which cleaves the phosphodiester bond after the A at A/G mismatches is added and incubated for 1 hr at 55° C. and 37° C. for the Tdg and mutY enzymes, respectively. In some cases, E. coli Endo IV is added to a set of Tdg enzyme tubes to facilitate phosphodiester bond cleavage at T/G mismatches where the Tdg enzyme has removed the T. At the end of the incubation, the tubes are incubated at 95° C. for 2 minutes to denature the partial cleavage products from the WT CS. The temperature is slowly decreased to 20° C. to allow more $^{32}$P-labelled MUT NCS probe to anneal to the target WT CS. More Tdg enzyme or mutY enzyme are added to the appropriate tubes and incubation is continued for 1 hour at 55° C. and 37° C., respectively. The cycle is then repeated. At the end of the final 1 hour incubation, loading buffer is added to the tubes. The DNA molecules are heat denatured and electrophoresed on a 20% denaturing polyacrylamide gel. The gel is exposed to X ray film, developed and analyzed.

EXAMPLE 4

Thermostable Enzyme Synthesis

Bacteria and Plasmids

Escherichia coli JM109 is available from New England Biolabs of Beverly, Mass. and Escherichia coli BW415 is available from the laboratory of Dr. Richard P. Cunningham at the State University of New York, at Albany, Department of Biological Sciences. A similar strain suitable for this protocol is BW434 and it is available from the Coli Genetic Stock Center at Yale University School of Medicine, New Haven, Conn.

BW415λDE3 was made with a λDE3 lysogenization kit from Novagen Inc. of Madison, Wis. This integration allowed for the efficient expression of the T/G mismatch specific thymine-DNA glycosylase from a T7 RNA polymerase driven promoter in an endonuclease III deficient strain of Escherichia coli. The expression system was contained on plasmid pET14B from Novagen Inc.

Plasmid pUV2 containing the orf10 coding sequence is available from Dr. Jork Nolling, Wageningen Agricultural University of the Netherlands, Department of Microbiology, Hesselink van Suchtelenweg 4, 6703 CT Wageningen, The Netherlands. The pUV2 plasmid contains a portion of pFV1, including the orf10 coding sequence, cloned into pUC19.

The methods for deriving plasmid pFV1 are disclosed in Nolling et al., Nuc. Acids Res. 20(24): 6501 (1992). Plasmid pUC19 is available from Sigma Chemical Co., of St. Louis, Mo.

Preparation and Manipulation of DNA

Plasmid DNA was prepared from JM109 by a modified alkaline lysis method. The orf10 coding sequence from pUV2 was cloned into pUC19 via a DraI-EcoRI to HincII-EcoRI ligation using restriction endonucleases and ligase (from New England Bio Labs) according to suppliers' recommendations. The gene was PCR mutagenized using Taq Polymerase from Perkin Elmer Corp. to simultaneously change a TTG start codon to ATG, create a NcoI restriction site (SEQ ID NO:7) (5' GTG GGG CTG GAT TTC CAT GGA TGA TGC TAC TAA T3' and also a BamHI site (SEQ ID NO:8) (5' C.GA CGG CCA GTG GAT CCA AGG GGG CTG ATG 3' outside the gene. These new restriction sites were used to clone orf10 into pET14B.

Enzyme Induction and Purification

This plasmid was transformed into Escherichia coli strain BW415λDE3 and selected from on ampicillin plates. Twenty four liters of cells were grown in Tryptone yeast (TY) broth supplemented with ampicilin at 37 C to an OD$_{595}$=0.5, and induced with 1 mM IPTG for five hours. The cells were harvested by centrifugation at 17,000×g for 20 minutes to yield 100.82 grams of cell paste which was stored at −80 C. The cell pellet was thawed, and suspended in 504 ml of 50 mM Tris-HCl pH 8.0, 200 mM NaCl, 2.5 mM EDTA 0.1 mM PMSF. The cell suspension was sonicated 5×3 minutes with a Branson sonifer, and then stirred on ice for one hour. The sonicate was centrifuged at 48,000×g for 20 minutes and the supernatant was retained. Five percent polyethelenimine was added to a final concentration of 0.1% and the suspension was stirred for 1 hour and centrifuged at 48,000×g to give a supernatant with a volume of 500 mls. The supernatant was dialyzed against 4 L of 50 mM KPO$_4$ pH 7.2 overnight.

The crude extract was loaded onto an 80 ml SP Sepharose® Fast Flow (Pharmacia Biotech Inc. of Piscataway, N.J.) column, washed with 100 ml of 50 mM KPO$_4$ pH 7.2 and eluted with a 1 L gradient from 0 to 1M NaCl at a flow rate of 10 ml/min. The protein eluted at 0.6M and a characteristic yellow color in the fractions indicative of an Fe-S cluster of the protein. The fractions containing the protein were pooled and dialyzed against 50 mM KPO$_4$ pH 6.6, loaded onto a 5 ml DNA agarose (Pharmacia Biotech Inc.) column, washed with 10 ml of 50 mM KPO$_4$ and eluted with a 100 ml gradient of 0–1 M NaCl at a rate of 1 ml/min. The protein eluted at 0.8M NaCl as determined by the criteria above. Fractions containing the protein were pooled and dialyzed overnight against 50 mM KPO$_4$pH 6.6. The protein was loaded onto a 5 ml SP high trap column (Pharmacia Biotech Inc.) and eluted with 1M NaCl to concentrate the protein. The extract was further concentrated to 1.5 mls with Centriprep® 10 concentrators (Amicon Division, W. R. Grace & Co., of Danvers, Mass.). At this point the protein was a single band on an overloaded Coomassie® stained gel and gave an $A_{410}/A_{280}$ ratio of 0.295. This protein was active in our T-G mismatch assay. The pure protein was stored in 50% glycerol at −20 C.

What is claimed is:

1. A method of detecting the presence of and determining the relative positions of at least two point mutations in a target polynucleotide, comprising:
   (a) hybridizing single-stranded oligonucleotide probes to a target polynucleotide to form hybrid, double-stranded polynucleotides such that mismatches occur at the sites of said point mutations, wherein said probes are complementary to a non-mutated sequence of said target polynucleotide and are labelled at one end but not both ends, and wherein said target polynucleotide is not labelled;
   (b) partially digesting the probe strand of said hybrid polynucleotide with a nucleic acid repair enzyme, wherein all possible recognition sites within the oligonucleotide probe are not cleaved and probe fragments of differing lengths are generated;
   (c) separating said probe fragments by size in a medium suitable for visualizing the separated probe fragments; and then
   (d) visualizing said separated probe fragments in said medium, whereby the presence and relative positions of said point mutations are determined.

2. The method of claim 1, comprising a further step of measuring the length of said separated probe fragments, thereby determining the specific nucleotide position of each point mutation.

3. The method of claim 1, wherein said partial digestion of step (b) is effected by a nucleic acid repair enzyme selected from the group consisting of muty, T/G mismatch-specific nicking enzyme, human or yeast all-type enzyme, and deoxyinosine 3'-endonuclease from E. coli.

4. The method of claim 1, wherein said partial digestion of step (b) comprises one or more additional nucleic acid repair enzymes selected from the group consisting of mutY, T/G mismatch-specific nicking enzyme, human or yeast all-type enzyme, and deoxyinosine 3'-endonuclease from E. coli.

5. The method of claim 1, wherein said partial digestion of step (b) is effected by a nucleic acid repair enzyme system comprising a glycosylase and a DNA lyase or a glycosylase and a DNA AP endonuclease.

6. The method of claim 1, wherein said partial digestion of step (b) is effected by a thermostable nucleic acid repair enzyme.

7. The method of claim 6, wherein said thermostable nucleic acid repair enzyme is thymine DNA glycosylase.

8. The method of claim 7, wherein said thymine DNA glycosylase comprises an ORF10 protein encoded by a DNA sequence comprising the sequence of Seq 9.

9. The method of claim 1, wherein said labeled probe of step (a) is radiolabelled.

10. The method of claim 1, wherein said separating of step (c) is accomplished by gel electrophoresis.

11. The method of claim 1, wherein said target polynucleotide is a cDNA sequence.

12. A method of detecting the presence of and determining the relative positions of at least two point mutations in a target polynucleotide, comprising:
   (a) hybridizing a single-stranded oligonucleotide probe to a target polynucleotide to form a hybrid, double-stranded polynucleotide such that mismatches occur at the sites of said point mutations, wherein said probe is complementary to a non-mutated sequence of said target polynucleotide and is labelled at one end but not both ends, and wherein said target polynucleotide is not labelled;
   (b) partially digesting the probe strand of said hybrid polynucleotide with a nucleic acid repair enzyme producing oligonucleotide fragments, wherein said oligonucleotide probe is designed such that said oligonucleotide fragments dissociate from said target polynucleotide spontaneously at a predetermined temperature;
   (c) repeating steps (a) and (b) such that probe fragments of differing lengths are generated;
   (d) separating said probe fragments by size in a medium suitable for visualizing the separated probe fragments; and then
   (e) visualizing said separated probe fragments in said medium, whereby the presence and relative positions of said point mutations are determined.

13. The method of claim 12, wherein said hybridization of step (a) is effectuated at a temperature which is approximately the same as said predetermined temperature of dissociation.

14. The method of claim 12, wherein said hybridization of step (a) is effectuated at a temperature which is lower than said predetermined temperature of dissociation.

15. The method of claim 12, comprising a further step of measuring the length of said separated probe fragments, thereby determining the specific nucleotide position of each point mutation.

16. The method of claim 12, wherein said partial digestion of step (b) is effected by a nucleic acid repair enzyme selected from the group consisting of muty, T/G mismatch-specific nicking enzyme, human or yeast all-type enzyme, and deoxyinosine 3'-endonuclease from E. coli.

17. The method of claim 12, wherein said partial digestion of step (b) comprises one or more additional nucleic acid repair enzymes selected from the group consisting of mutY, T/G mismatch-specific nicking enzyme, human or yeast all-type enzyme, and deoxyinosine 3'-endonuclease from E. coli.

18. The method of claim 12, wherein said partial digestion of step (b) is effected by a nucleic acid repair enzyme system comprising a glycosylase and a DNA lyase or a glycosylase and a DNA AP endonuclease.

19. The method of claim 12, wherein said partial digestion of step (b) is effected by a thermostable nucleic acid repair enzyme.

20. The method of claim 19, wherein said thermostable nucleic acid repair enzyme is thymine DNA glycosylase.

21. The method of claim 20, wherein said thymine DNA glycosylase comprises an ORF10 protein encoded by a DNA sequence comprising the sequence of Seq. 9.

22. The method of claim 12, wherein said labeled probe of step (a) is radiolabelled.

23. The method of claim 12, wherein said separating of step (d) is accomplished by gel electrophoresis.

24. The method of claim 12, wherein said target polynucleotide is a cDNA sequence.

25. The method of claim 12, wherein a heat destabilization molecule is added to said hybridizing of step (a), such that the temperature of hybridization is decreased.

* * * * *

SEQUENCE LISTING

```
<160> NUMBER OF SEQ ID NOS: 10

<210> SEQ ID NO 1
<211> LENGTH: 15
<212> TYPE: PRT
<213> ORGANISM: Unknown Organism
<220> FEATURE:
<223> OTHER INFORMATION: Description of Unknown Organism: Unknown
      endonuclease

<400> SEQUENCE: 1

Pro Tyr Val Ile Leu Ile Thr Glu Ile Leu Leu Arg Arg Thr Thr
1               5                   10                  15

<210> SEQ ID NO 2
<211> LENGTH: 12
<212> TYPE: PRT
<213> ORGANISM: Unknown Organism
<220> FEATURE:
<223> OTHER INFORMATION: Description of Unknown Organism: Unknown
      endonuclease

<400> SEQUENCE: 2

Ala Ile Leu Asp Leu Pro Gly Val Gly Lys Tyr Thr
1               5                   10

<210> SEQ ID NO 3
<211> LENGTH: 12
<212> TYPE: PRT
<213> ORGANISM: Unknown Organism
<220> FEATURE:
<223> OTHER INFORMATION: Description of Unknown Organism: Unknown
      endonuclease

<400> SEQUENCE: 3

Met Val Asp Ala Asn Phe Val Arg Val Ile Asn Arg
  1               5                   10

<210> SEQ ID NO 4
<211> LENGTH: 75
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 4
aaatggagtt attccaacag ataaagtgtt gaatggaata cttagttatc ttggaatgac      60
```

-continued taaagtagaa ttaga                                                          75

<210> SEQ ID NO 5
<211> LENGTH: 74
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 5
tctaattcta ctttagtaat tccaagataa ttaagtatcc attaaacact ttatttgttg         60
gaataactcc attt                                                           74

<210> SEQ ID NO 6
<211> LENGTH: 75
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 6
tctaatttta ctttagtaat tccaagataa ttaagtattc catttaacac tttatatgtt         60
ggaataattc cattt                                                          75

<210> SEQ ID NO 7
<211> LENGTH: 34
<212> TYPE: DNA
<213> ORGANISM: Unknown Organism
<220> FEATURE:
<223> OTHER INFORMATION: Description of Unknown Organism: NcoI
      restriction site

<400> SEQUENCE: 7
gtggggctgg atttccatgg atgatgctac taat                                     34

<210> SEQ ID NO 8
<211> LENGTH: 30
<212> TYPE: DNA
<213> ORGANISM: Unknown Organism
<220> FEATURE:
<223> OTHER INFORMATION: Description of Unknown Organism: BamHI site

<400> SEQUENCE: 8
cgacggccag tggatccaag ggggctgatg                                          30

<210> SEQ ID NO 9
<211> LENGTH: 666
<212> TYPE: DNA
<213> ORGANISM: Unknown Organism
<220> FEATURE:
<223> OTHER INFORMATION: Description of Unknown Organism: ORF 10
<221> NAME/KEY: CDS
<222> LOCATION: (1)..(663)

<400> SEQUENCE: 9 atg gat gat gct act aat aaa aaa agg aaa gtc ttc gtt agc acc ata           48
Met Asp Asp Ala Thr Asn Lys Lys Arg Lys Val Phe Val Ser Thr Ile
  1               5                  10                  15 ctt acg ttt tgg aat aca gat agg cgc gac ttt cct tgg agg cat acg           96
Leu Thr Phe Trp Asn Thr Asp Arg Arg Asp Phe Pro Trp Arg His Thr
             20                  25                  30 agg gac ccc tat gta att tta ata cg gaa atc cta ctt cgc agg aca          144

-continued

```
                Arg Asp Pro Tyr Val Ile Leu Ile Thr Glu Ile Leu Leu Arg Arg Thr
                            35                  40                  45 act gcg ggg cat gtt aaa aag ata tat gac aag ttt ttt gtt aag tac         192
Thr Ala Gly His Val Lys Lys Ile Tyr Asp Lys Phe Phe Val Lys Tyr
 50                  55                  60 aag tgc ttt gag gat ata tta aaa acg cca aaa tca gaa atc gcc aaa         240
Lys Cys Phe Glu Asp Ile Leu Lys Thr Pro Lys Ser Glu Ile Ala Lys
 65                  70                  75                  80 gac ata aaa gaa atc gga ctc tct aac caa agg gca gaa cag cta aaa         288
Asp Ile Lys Glu Ile Gly Leu Ser Asn Gln Arg Ala Glu Gln Leu Lys
                 85                  90                  95 gaa ctg gca agg gtc gtc ata aat gat tat ggg gga aga gtg ccc cga         336
Glu Leu Ala Arg Val Val Ile Asn Asp Tyr Gly Gly Arg Val Pro Arg
             100                 105                 110 aat agg aag gca att tta gat cta cca gga gtt ggc aaa tac act tgt         384
Asn Arg Lys Ala Ile Leu Asp Leu Pro Gly Val Gly Lys Tyr Thr Cys
             115                 120                 125 gct gca gtt atg tgt ttg gca ttt ggc aaa aaa gcc gct atg gtc gat         432
Ala Ala Val Met Cys Leu Ala Phe Gly Lys Lys Ala Ala Met Val Asp
         130                 135                 140 gca aat ttt gtg aga gtt att aac agg tac ttt ggg gga agc tat gaa         480
Ala Asn Phe Val Arg Val Ile Asn Arg Tyr Phe Gly Gly Ser Tyr Glu
145                 150                 155                 160 aac ctg aac tac aac cac aag gcc ctg tgg gaa ctt gcg gag acc ctt         528
Asn Leu Asn Tyr Asn His Lys Ala Leu Trp Glu Leu Ala Glu Thr Leu
                 165                 170                 175 gta cct ggc gga aag tgc agg gac ttt aac ctt ggt tta atg gac ttt         576
Val Pro Gly Gly Lys Cys Arg Asp Phe Asn Leu Gly Leu Met Asp Phe
             180                 185                 190 tcc gca atc ata tgt gcc cca aga aag cca aag tgt gag aaa tgt ggg         624
Ser Ala Ile Ile Cys Ala Pro Arg Lys Pro Lys Cys Glu Lys Cys Gly
             195                 200                 205 atg agc aaa ctc tgt agc tac tat gag aag tgt agt act tga               666
Met Ser Lys Leu Cys Ser Tyr Tyr Glu Lys Cys Ser Thr
         210                 215                 220
```

<210> SEQ ID NO 10
<211> LENGTH: 221
<212> TYPE: PRT
<213> ORGANISM: Unknown Organism
<220> FEATURE:
<223> OTHER INFORMATION: Description of Unknown Organism: ORF 10

<400> SEQUENCE: 10

```
Met Asp Asp Ala Thr Asn Lys Lys Arg Lys Val Phe Val Ser Thr Ile
 1               5                  10                  15

Leu Thr Phe Trp Asn Thr Asp Arg Arg Asp Phe Pro Trp Arg His Thr
                 20                  25                  30

Arg Asp Pro Tyr Val Ile Leu Ile Thr Glu Ile Leu Leu Arg Arg Thr
             35                  40                  45

Thr Ala Gly His Val Lys Lys Ile Tyr Asp Lys Phe Phe Val Lys Tyr
         50                  55                  60

Lys Cys Phe Glu Asp Ile Leu Lys Thr Pro Lys Ser Glu Ile Ala Lys
 65                  70                  75                  80

Asp Ile Lys Glu Ile Gly Leu Ser Asn Gln Arg Ala Glu Gln Leu Lys
                 85                  90                  95

Glu Leu Ala Arg Val Val Ile Asn Asp Tyr Gly Gly Arg Val Pro Arg
             100                 105                 110

Asn Arg Lys Ala Ile Leu Asp Leu Pro Gly Val Gly Lys Tyr Thr Cys
```

-continued

```
                    115                 120                 125
Ala Ala Val Met Cys Leu Ala Phe Gly Lys Lys Ala Ala Met Val Asp
        130                 135                 140
Ala Asn Phe Val Arg Val Ile Asn Arg Tyr Phe Gly Gly Ser Tyr Glu
145                 150                 155                 160
Asn Leu Asn Tyr Asn His Lys Ala Leu Trp Glu Leu Ala Glu Thr Leu
                165                 170                 175
Val Pro Gly Gly Lys Cys Arg Asp Phe Asn Leu Gly Leu Met Asp Phe
            180                 185                 190
Ser Ala Ile Ile Cys Ala Pro Arg Lys Pro Lys Cys Glu Lys Cys Gly
        195                 200                 205
Met Ser Lys Leu Cys Ser Tyr Tyr Glu Lys Cys Ser Thr
    210                 215                 220
```